United States Patent [19]

Repke et al.

[11] 4,205,679
[45] Jun. 3, 1980

[54] DISPOSABLE UNDERGARMENT

[75] Inventors: Virginia L. Repke, Oak Forest; Ralph H. Brooks, Jr., Palos Heights, both of Ill.

[73] Assignee: Johnson & Johnson, New Brunswick, N.J.

[21] Appl. No.: 898,374

[22] Filed: Apr. 20, 1978

Related U.S. Application Data

[63] Continuation-in-part of Ser. No. 707,972, Jul. 23, 1976, abandoned.

[51] Int. Cl.² .......................................... A61F 13/16
[52] U.S. Cl. .................................................. 128/287
[58] Field of Search ............... 128/283, 287, 284, 290, 128/290 R, 290 W

[56] References Cited
U.S. PATENT DOCUMENTS

| | | | |
|---|---|---|---|
| 2,905,581 | 9/1957 | Maxey | 128/288 X |
| 3,088,402 | 5/1963 | Muto | 128/288 X |
| 3,232,293 | 2/1966 | DeWoskin | 128/288 |
| 3,237,625 | 3/1966 | Johnson | 128/288 |
| 3,332,423 | 7/1967 | Whalen | 128/288 |
| 3,599,638 | 8/1971 | Rickard | 128/288 |
| 3,613,686 | 10/1971 | DeWoskin | 128/288 |
| 3,613,687 | 10/1971 | Kennedy | 128/288 |
| 3,814,101 | 6/1974 | Kozak | 128/287 |
| 3,828,784 | 8/1974 | Zoephel | 128/288 |
| 3,828,785 | 8/1974 | Gamm | 128/288 |
| 3,885,568 | 5/1975 | Schaar | 128/288 |
| 3,890,973 | 6/1975 | Davis et al. | 128/287 X |
| 3,990,450 | 11/1976 | Schaar | 128/287 |
| 4,036,233 | 7/1977 | Kozak | 128/290 X |
| 4,050,462 | 9/1977 | Woon et al. | 128/287 |

FOREIGN PATENT DOCUMENTS 780086 3/1968 Canada ...................................... 128/284

*Primary Examiner*—Robert W. Michell
*Assistant Examiner*—Milford Juten
*Attorney, Agent, or Firm*—Robert L. Minier

[57] ABSTRACT

A unitary, multi-layer disposable undergarment such as a panty adapted for use in training infants or for use by incontinent adults or children is provided. The undergarment is constructed from a non-woven, stretchable fabric and comprises a front portion, a rear portion, a crotch portion, a self-fitting waist portion and self-fitting leg apertures. The preferred undergarment has an inner ply of stretchable fabric adapted to contact an infant's skin, a moisture-impervious or mositure retardant outer ply and an intermediate liquid-absorbent layer or panel disposed therebetween. The inner and outer plies preferably are constructed from a non-woven fabric which has been mechanically compressed to provide small pleats (micropleats) perpendicular to the machine direction and which has first been compacted in the cross direction to provide the desired stretch characteristics. The inner and outer plies are formed from substantially hour-glass shaped blanks having longitudinally oblong side cut-outs which blanks are cut from the micropleated, cross-compacted web so that the micropleats are disposed in the longitudinal direction of the blank to provide the desired stretch in the leg and crotch area.

40 Claims, 25 Drawing Figures

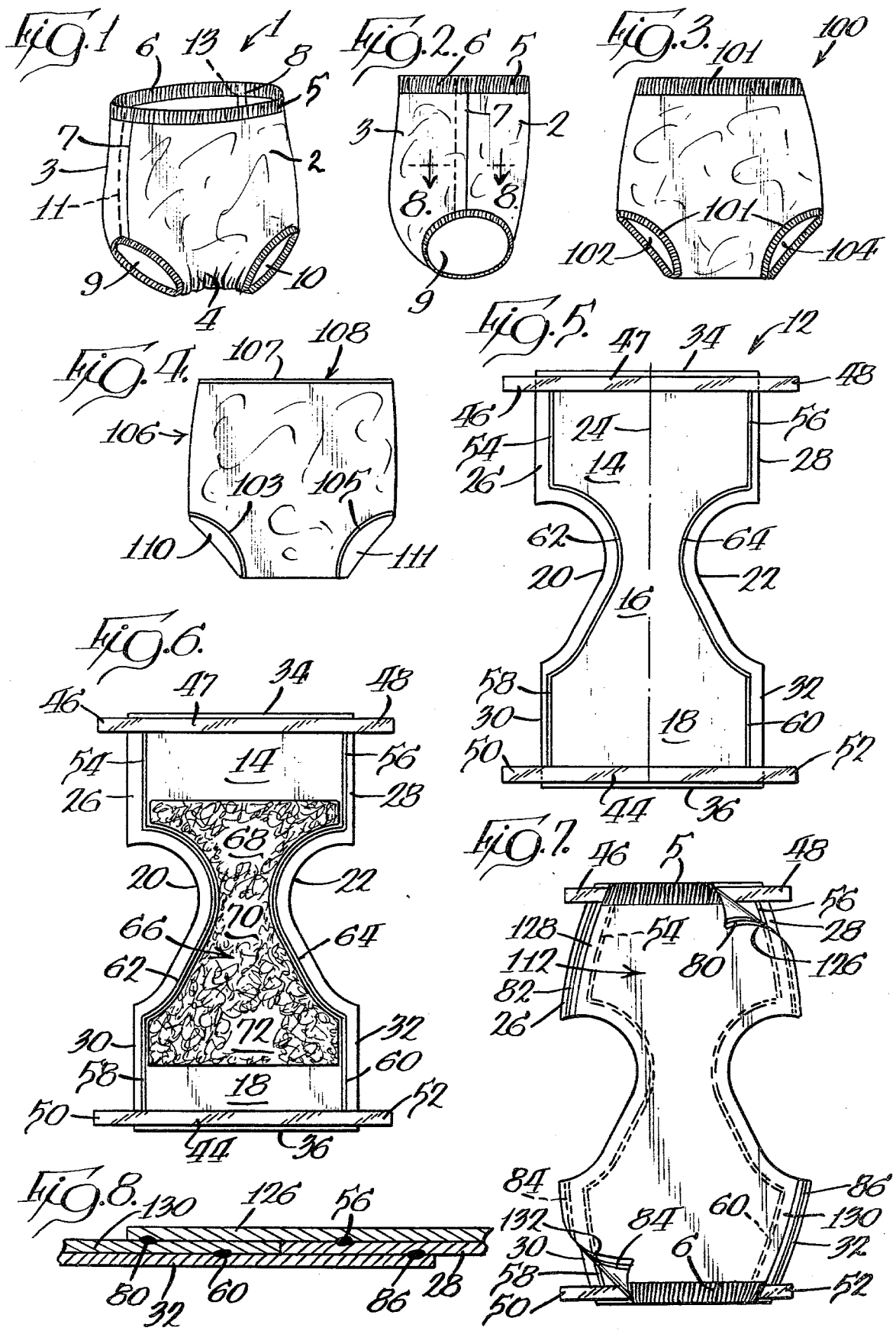

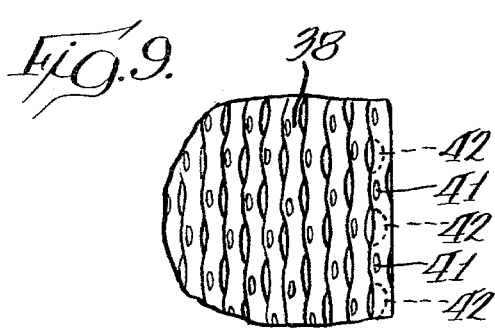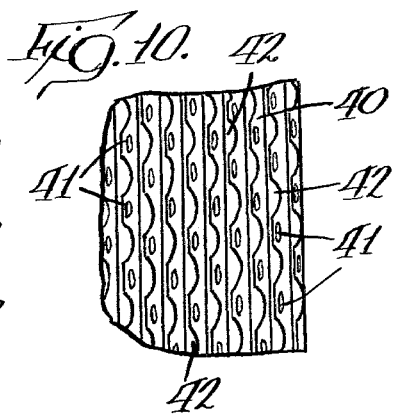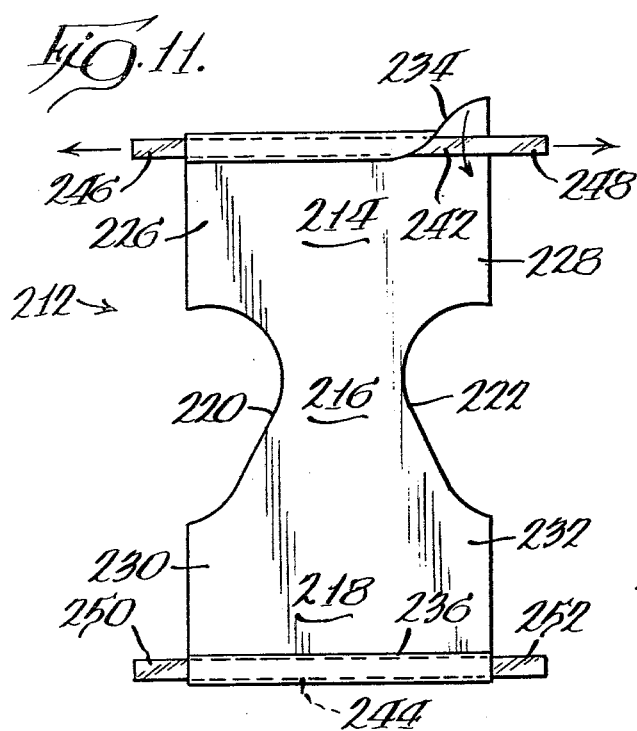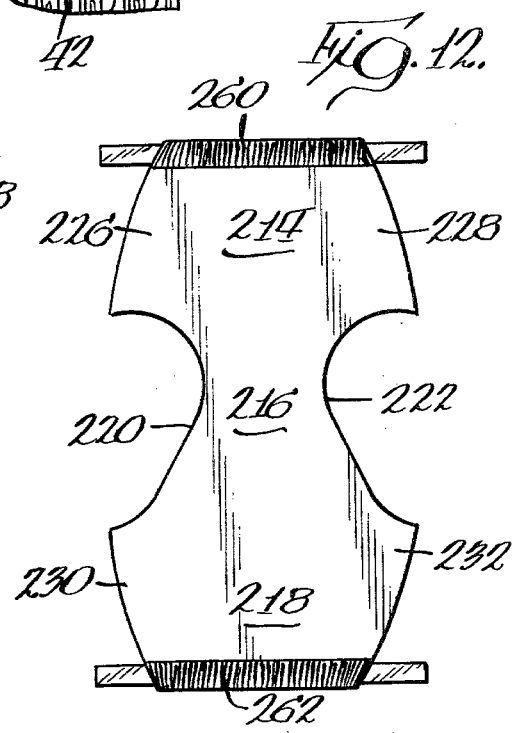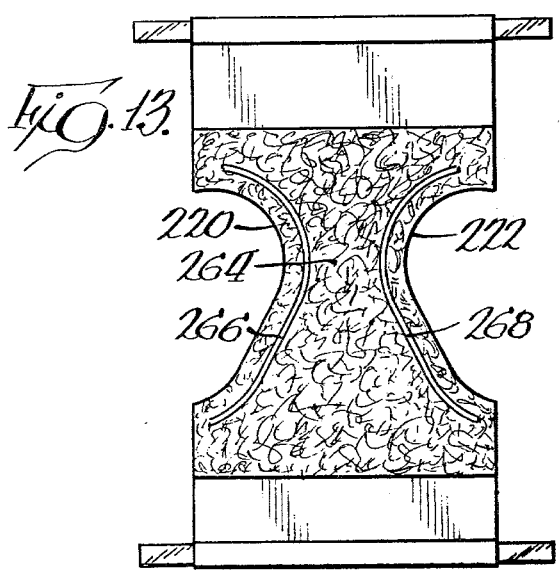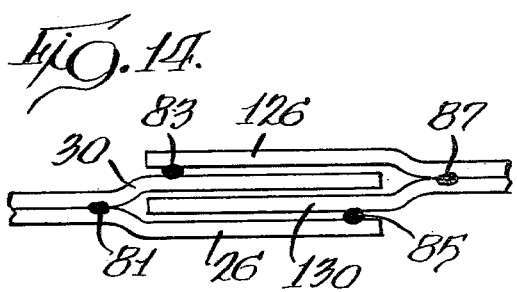

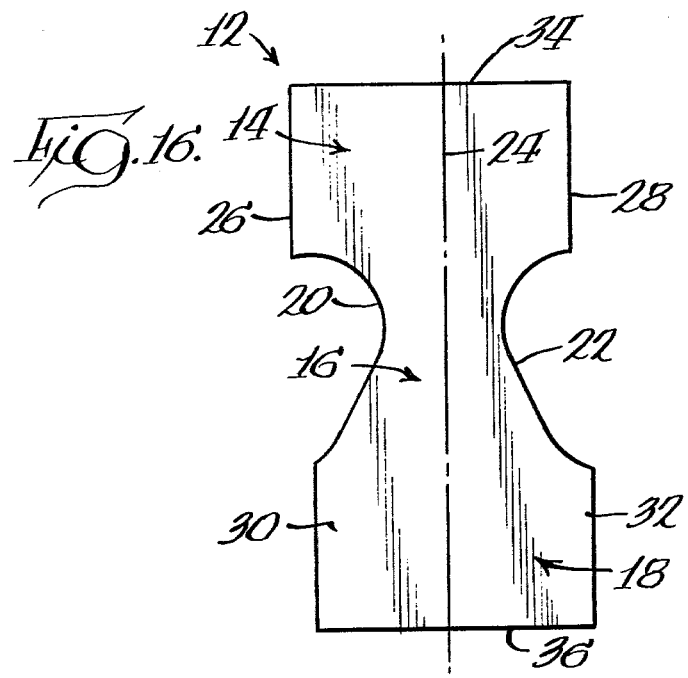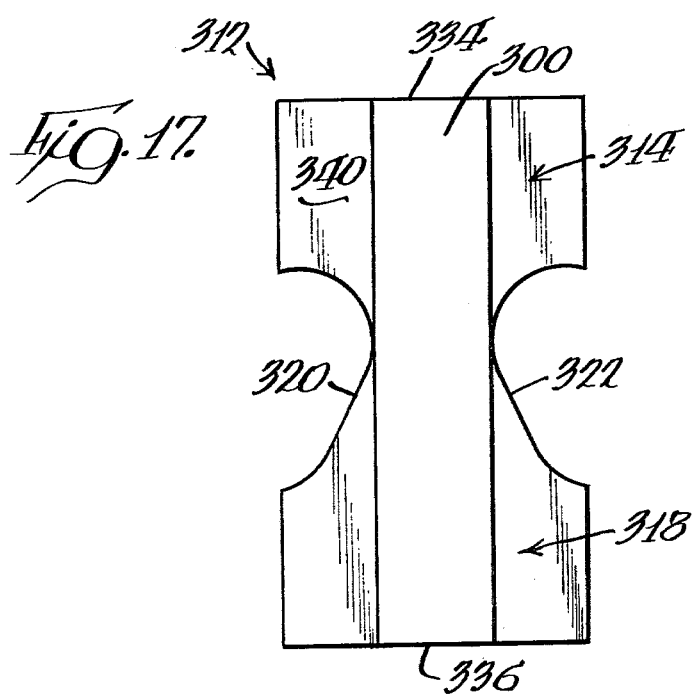

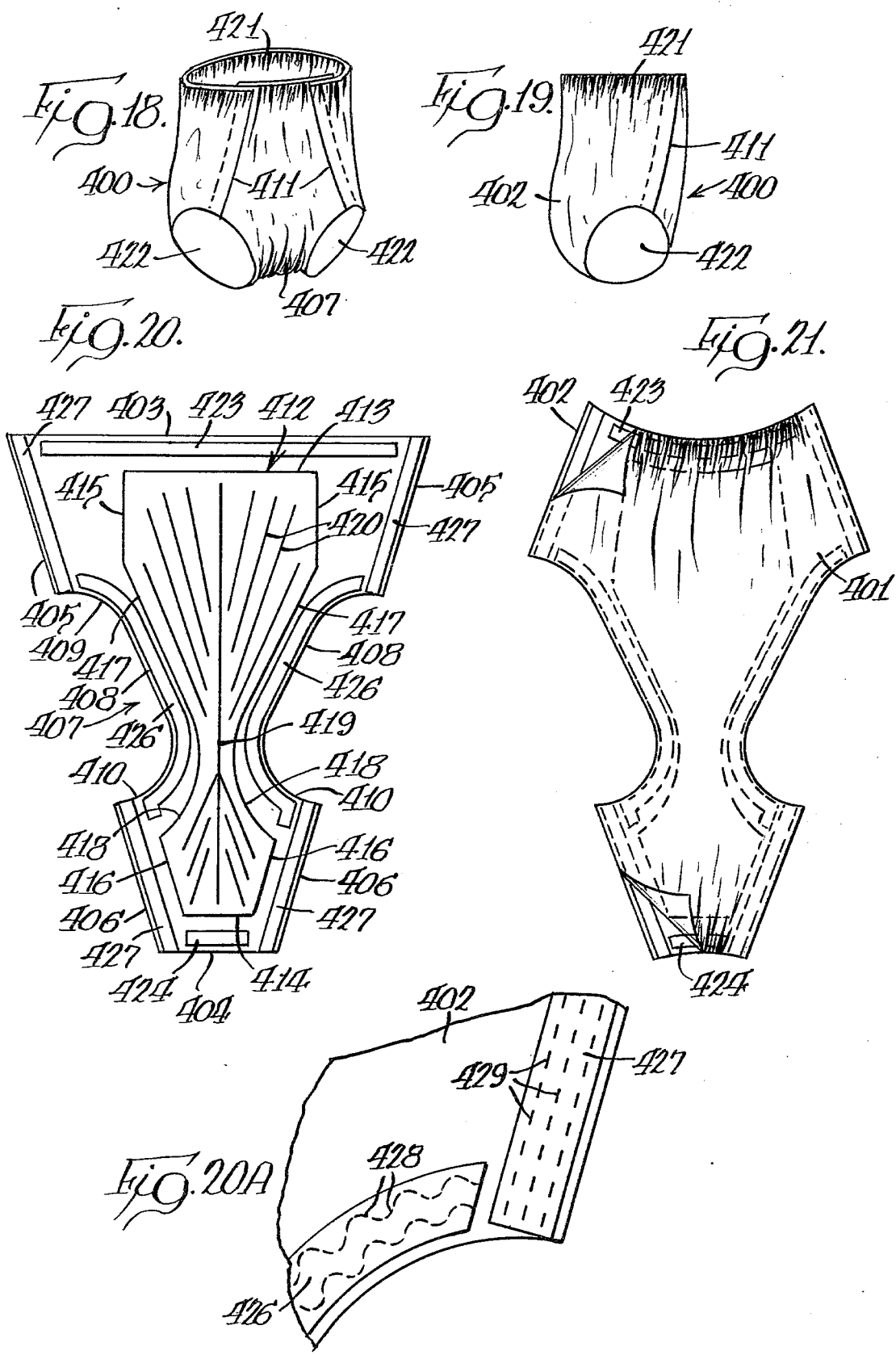

DISPOSABLE UNDERGARMENT

CROSS REFERENCE TO RELATED APPLICATION

This application is a continuation-in-part of abandoned application Ser. No. 707,972 filed July 23, 1976.

BACKGROUND OF THE INVENTION

In recent years, disposable diapers have met with increased commercial acceptance primarily because of their convenience as opposed to cloth diapers which need to be laundered once soiled. There exists, however, a need for a disposable training panty which can be used during the transition period between diapers and reusable undergarments. An undergarment of this general type would also be useful with incontinent adults and children because of their absorbent properties, fit, and disposability.

Currently available training pants are generally made from knitted or woven cloth, such as cotton, or cotton-polyester blends. They may or may not include additional absorbent layers in the crotch area and they may include a water-repellent outer layer. Non-disposable training pants are disclosed, for example, in U.S. Pat. Nos. 2,733,715; 3,237,625; 3,368,563; 3,530,859; and 3,613,687.

The prior art and commercially available training pants suffer from a number of disadvantages, however. Aside from the obvious disadvantage of having to be laundered, the primary disadvantage of the currently available conventional cloth training panty is the problem of liquid strike-through. The prior art has attempted to solve this problem by providing areas of extra absorbency utilizing, for example, terrycloth or a piled fabric in the crotch portion of the panty and/or additionally including a water-repellent outer layer in the crotch area, or over the entire outer surface of the panty. However, as anyone known who has ventured through the traumatic training period with their babies, the prior art simply has not provided a satisfactory solution.

For the above reasons, many mothers continue to use diapers during the training period, rather than suffer the annoyance of liquid strike-through when their child has an accident. While the use of diapers substantially reduces the problem of liquid strike-through, diaper use during the training period is highly undesirable and tends to prolong the period required to completely train the child. Psychollogically, it is desirable for children to be in panties during the training period so they are aware of no longer being babies and are more aware of accidents.

Aside from the undesirable psychological drawbacks of continuing to use diapers during the training period, disposable diapers present an economic drawback. Disposable diapers generally utilize tape tab fasteners in place of safety pins as fastening means. When the tabs are removed so that the child can be placed on the toilet, the unsoiled diaper must be discarded because the currently available tabs are for a single use fonly and usually tear the backing fabric when they are pulled away.

A variety of disposable panties are known. See, for example, U.S. Pat Nos. 3,424,162; 3,599,638; 3,599,640; and 3,636,953. Such panties are provided with or adapted to receive a sanitary napkin in the crotch portion of the panty and are not adapted to deal with the liquid strike-through problem encountered during the training period or with incontinent adults or children. Similarly, the disposable panty types disclosed in U.S. Pat. Nos. 3,663,962; 3,245,407 and 3,488,778, do not satisfy the need for a disposable training panty, because the panties are either nonabsorbent, such as plastic, or lack the necessary fit in the leg and waist area to prevent the problem of liquid strike-through and leakage.

SUMMARY OF THE INVENTION

The disposable undergarment of this invention, on the other hand, is particularly well adapted to be used as a training panty during the training period. The undergarment is constructed of one or more plies of stretchable non-woven fabric. Preferably, several plies of stretchable, non-woven fabric are utilized to provide different absorption and moisture-permeability characteristics for the inner and the outer layer of the undergarment, as well as good conformability and fit without attendant bulkiness. The inner, or facing, layer of the undergarment provides an innermost ply having a soft surface for contact with the wearer's skin, readily permits passage of excreted body liquids therethrough, and can provide an absorbent mass for body liquids as well, if desired. The outer, or backing, layer of the undergarment, on the other hand, presents at least one ply which is an effective liquid barrier and which prevents or substantially minimizes body liquid strike-through. In a preferred embodiment of this invention, the non-woven outer fabric layer, as well as the non-woven inner fabric layer, are micropleated in the machine direction of the fabric and compacted in the cross-direction of the fabric to give enhanced stretch or extensibility characteristics.

The preferred disposable undergarment comprises two stretchable, non-woven fabric layers having one or more plies each, preferably compressively-shrunk non-woven fabrics, and an absorbent layer or penel which is disposed between the inner and outer layers at least in the crotch portion of the undergarment. If desired, the absorbent layer can extend further up the back and/or the front portions of the undergarment. The undergarment has a self-fitting waist aperture and self-fitting leg apertures.

Fabric blanks for manufacturing the undergarment of this invention are laid out and cut to provide a substantially hour-glass shape of which one end panel is adapted to become the front portion of the undergarment, another end panel is adapted to become the back or rear portion of the undergarment, and an intermediate region of the blank is adapted to become the crotch portion of the undergarment. Longitudinally oblong portion of the blank provide leg apertures when an undergarment is formed from the blank. Elasticity can be imparted to the waistband portion of the undergarment by the use of a thermoplastic, heat-sealable elastic material which can be laid down along the waistband region of the blank, stretched, retained in a stretched condition during heat-sealing, and then allowed to relax after the heat-sealing process, gathering at least a portion of the fabric in the waistband region. Fit in the waistband area and the leg area is enhanced by cutting the blanks from a cross-compacted and micropleated fabric so that the micropleats run parallel to the longitudinal center line of the blank, that is, from one waistband edge to the other waistband edge, and the compaction runs substantially parallel to the micropleats, i.e., substantially normal to the machine direction of the fabric web during micropleating.

A further feature of the preferred disposable undergarments of this invention is the seam construction for joining the front and back portions of the undergarment to form the waist aperture and the leg apertures. According to this feature, side margins of a pair of superimposed blanks are overlapped and joined so that the seam comprises only three ply thicknesses at any given location along the seam. That is, in the overlapping region, one of the outer plies abuts one of the inner plies while the other outer ply and the other inner ply extend from opposite sides over the abutting plies.

The resulting product not only provides an undergarment which minimizes liquid strike-through problems while at the same time improving fit around the waist and leg areas, but does so with a novel arrangement of components which give the feel of a more costly cloth garment while being sufficiently inexpensive to be disposed of after a single use. Thus, the garment of the present invention solves many of the problems inherent in the past, and constitutes a significant advance in the art.

BRIEF DESCRIPTION OF THE DRAWINGS

The present invention will be further illustrated by reference to the following detailed description taken in conjunction with the accompanying drawings in which:

FIG. 1 is a perspective view of a disposable training panty embodying this invention;

FIG. 2 is a side elevational view of the disposable training panty illustrated in FIG. 1;

FIG. 3 is a front elevational view of another embodiment of the disposable training panty of this invention;

FIG. 4 is a further embodiment of the disposable training panty of this invention;

FIG. 5 is a plan view of an assembly used to form the training panty illustrated in FIGS. 1 and 2;

FIG. 6 is a plan view of an assembly used to form the training panty of FIGS. 1 and 2 and having an absorbent layer or panel positioned in the crotch area thereof;

FIG. 7 is a plan view of an assembly utilizing two superimposed blanks used to form the training panty of FIGS. 1 and 2 after the leg and waist portions have been joined in a stretchable fashion, with parts of the uppermost blank folded away to show interior construction;

FIG. 8 is a cross-sectional view of the side seam portion of the disposable training panty taken along plane 8—8 of FIG. 2;

FIG. 9 is an enlarged view of the front surface of the preferred fabric used in constructing the training panty of this invention;

FIG. 10 is an enlarged view of the back surface of the fabric of FIG. 9;

FIG. 11 is a plan view of an assembly used to form an embodiment of the disposable training panty of this invention wherein the waistband portion of the blank has been folded over a heat-sealable, stretchable material;

FIG. 12 is a plan view of the assembly of FIG. 11 after the waistband portions have been sealed;

FIG. 13 is a view of an assembly similar to that shown in FIG. 11 and additionally having an absorbent layer or panel sealed at the leg portions to the single blank;

FIG. 14 is a cross-sectional view of another suitable side seam construction;

FIG. 15 is an end view of yet another side seam construction that can be utilized;

FIG. 16 is a plan view of paired blanks suitable for manufacture of an undergarment embodying the present invention;

FIG. 17 is a plan view of an alternate embodiment of an assembly utilized to form a panty of this invention;

FIG. 18 is a perspective view of still another embodiment of the disposable training panty of this invention;

FIG. 19 is a side elevation view of the disposable training panty illustrated in FIG. 18;

FIG. 20 is a plan view of an assembly used to form the training panty illustrated in FIG. 18;

FIG. 20A is an enlarged plan view of the assembly shown in FIG. 20;

FIG. 21 is a plan view of an assembly utilizing two superimposed blanks used to form the training panty of FIG. 18, with portions of the uppermost blank folded away to show interior construction.

DETAILED DESCRIPTION OF THE PREFERRED EMBODIMENT

Figure 22A:
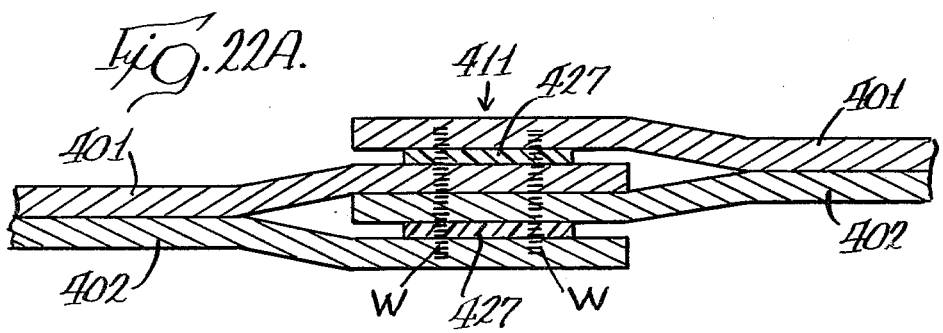
FIG. 22 a, b, and c are cross-sectional views through suitable side seam constructions for the training panty embodiment illustrated in FIG. 18.

Referring now to the drawings, there is shown a disposable training panty which is adapted to be used during the training period of an infant. Baby training panty 1 is perferably constructed from a light-weight, non-woven fabric formed predominantly of short-length cellulosic fibers with a minor percentage of long fibers in a non-woven web of the type disclosed in U.S. Pat. No. 3,663,348 to Liloia et al. Other non-woven webs that can be used are the so-called transition webs manufactured by the process disclosed in U.S. Pat. No. 3,768,118 to Ruffo et al. Other suitable webs are carded or spun-bonded long-fiber non-woven webs such as those disclosed in U.S. Pat. No. 3,815,602. It is preferred that thermoplastic fibers be included in the webs, so that the undergarment may be assembled by heat sealing techniques, as will hereinafter appear.

Prior to being cut into a blank suitable for use in the construction of the baby panty of this invention, the non-woven web can be made stretchable by compressive shrinking, preferably by compacting the fabric in the cross direction and micropleating in the machine direction, so that the extensibility to rupture preferably is at least about 30 percent, and more preferably greater that about 55 percent, in the machine direction, and preferably at least about 40 percent, and more preferably greater than about 60 percent, in the cross direction. Such a fabric will be hereinafter referred to as a compressively-shrunk fabric.

Compressively shrunk non-woven fabrics can be made by subjecting a non-woven fabric web to creping, micropleating, rubber felt compressing, or compacting in either the machine direction or the cross direction of the fabric. For optimum stretchability or extensibility, the fabric web can be subjected to a combination of two or more of the aforementioned treatments. For the purposes of the present invention a particularly preferred compressively shrunk fabric is one which has been compacted in the cross direction by passage through nested bowed rolls of the type shown in U.S. Pat. No. 3,171,579 to Robertson and thereafter micropleated according to the teachings of U.S. Pat. No. 3,390,218 to Painter et al. and U.S. Pat. No. 3,556,921 to Painter et al. After micropleating, the compressively shrunk fabric exhibits a plurality of discontinuous pleats across the width of the fabric, which pleats are made up of relatively smaller pleats interrupted in the transverse direction of the fabric by relatively larger pleats. When used in the products of this invention, the micropleated compressively shrunk fabric is turned 90° from the machine direction, and as can be seen from FIGS. 9 and 10, a pleat pattern of relatively smaller pleats 41 and relatively larger pleats 42 extends across the fabric length, each of the relatively larger pleats having adjacent thereto a relatively smaller pleat both in the longitudinal and in the transverse directions. Stated in another way, each relatively longer pleat is separated from nearest pleat of substantially the same size by a relatively smaller pleat. One surface of the micropleated web is puffed surface 40 and the other surface is ribbed surface 38 having a relatively softer hand. Micropleated fabrics generally have about 8 to about 20 rows of micropleats per inch.

Referring to FIGS. 1 and 2, in the preferred embodiment, baby training panty 1 is a multi-layered construction having a front portion 2, a rear portion 3, crotch portion 4, front waistband section 5 and rear waistband section 6 which together form a self-fitting waistband, side seams 7 and 8, and self-fitting leg apertures 9 and 10. Side seams 7 and 8 are secured by securement lines such as glue lines 11 and 13, respectively.

Baby training panty 1 is constructed from paired superimposed fabric blanks such as stretchable integral blank 12 which is shown in FIG. 16 to be a rectangular member having a length dimension greater than the width dimension. As will hereinafter appear, the paired blanks 12 form the inner and outer layers of the panty garment, and both blanks are identical in size and shape. The configuration of each blank 12 defines front panel 14, back panel 18 and crotch portion 16 therebetween. Longitudinally oblong opposed cut-outs 20 and 22 form leg apertures 9 and 10 of panty 1. Cut-outs 20 and 22 are positioned on opposite side of longitudinal center line 24 of blank 12 and extend from front panel 14 to back panel 18 on each longitudinal side of the blank and define the side edges of crotch portion 16. The radium of curvature of cut-outs 20 and 22 near front panel 14 is smaller than the radius of curvature near back panel 18.

Front and back panels or portions 14 and 18 of each of the two blanks are substantially the same width and are asymmetric, having unequal distances from opposite side edges of each portion to the longitudinal center line of the blanks. That is, the distance from the side edge of front portion longitudinal side margin 26 to the longitudinal center line 24 of blank 12 is greater than the distance from the side edge of opposed front portion longitudinal side margin 28 to center line 24. Similarly, the distance from the side edge of back portion side margin 30 to longitudinal center line 24 is less than the distance from the side edge of opposed back portion side margin 32 to center line 24.

Stated in another way, the distance from the side edge margin 26 to center line 24 is greater than the distance from the side edge of margin 30 to center line 24 and the distance from the side edge of margin 28 to center line 24 is less than the distance from the side edge of margin 32 to center line 24. Blank 12 can also be characterized as having front panel or portion 14 and the back or rear panel or portion 18 asymmetrically positioned with respect to the longitudinal center line 24 of the blank. Such an arrangement provides the unique seam construction illustrated in FIG. 8 and discussed hereinbelow.

Blank 12 additionally defines front waistband edge 34 and back waistband edge 36.

In order to provide the desired stretch in the waistband area, blank 12 is cut from a micropleated, cross-compacted non-woven fabric web so that the micropleats preferably run along, i.e., substantially parallel to, longitudinal center line 24 of the blank and the cross-compaction runs substantially normal to the direction of micropleating. The blanks are cut in this manner for optimum stretch and fit in the leg area.

Referring now to FIGS. 5, 9 and 10, in constructing panty 1, blank 12 is positioned so that ribbed surface 38 (FIG. 9) of one face of the micropleated, cross-compacted fabric faces downwardly and puffed surface 40 (FIG. 10) formed during micropleating on the other face of the fabric faces upwardly.

Strip 47 of an elastomeric material such as an elastic natural rubber tape (e.g., L-1900 rubber compound which is commercially available from Easthampton Rubber Tread Company) is disposed along front waistband transverse edge 34 of blank 12 and strip 44 of a like elastomeric material is disposed along back waistband transverse edge 36. Strips 44 and 47 are stretched and then secured in place on the blank by, for example, elastomeric double-sided transfer tape, such as No. 465 high-tack pressure-sensitive tape available from the Minnesota Mining and Manufacturing Co., St. Paul, Minnesota.

Alternatively, and preferably, stretch is provided in the waistband by utilizing strips or extruded beads of thermoplastic elastomeric materials such as heat-sealable, elastomeric block copolymers of styrene and isoprene or a similar diene. Materials of this general type are commercially available from Shell Chemical Company under the designation "Kraton". Similarly, elastomeric strips of the polyolefin type disclosed in U.S. Pat. No. 3,245,407 to Mason and elastomeric strips of the type disclosed in U.S. Pat. No. 3,639,917 to Althouse can also be utilized. Also suitable are flexible heat-shrinkable polyurethane strips of the type shown in U.S. Pat. No. 3,912,565 to Koch et al.

Before blanks 12 and 112 are superimposed, adhesive beads or strips 54, 56, 58 and 60 are deposited along the transverse axis of the blank substantially parallel to the outer margins 26, 28, 30 and 32, respectively, of blank 12. The two blanks are then secured together along the glue lines depicted in FIG. 5, for ease of manufacture preferably prior to forming the heat-sealed waistband areas 5 and 6. Side seams 7 and 8 of panty 1 can be formed as described hereinbelow.

The fit in the leg area can be further enhanced by extruding or otherwise suitably depositing beads of hot-melt elastic 62 and 64 as shown in FIG. 5. Suitable for this purpose are aforementioned thermoplastic elastomeric compositions commercially available from Shell Chemical Company under the designation "Kraton".

Glue lines 54 and 56 are extruded onto adjacent longitudinal front panel side margins 26 and 28 of blank 12, respectively. Similarly glue lines 58 and 60 are deposited adjacent longitudinal back panel side margins 30 and 32, respectively, to secure another blank over blank 12 when a multilayer garment is manufactured. The same set of glue lines is used to secure both blanks together, thus there is no need for an additional set of glue lines on the superimposed blank. Beads 62 and 64 of a hot-melt elastomeric material or the like (e.g., elastomeric block copolymers of styrene and isoprene) can be laid down along the margins of oblong cut-outs 20 and 22 to provide a gasketing effect and to enhance fit in the leg area. Glue lines 58 and 60 and gasketing beads 62 and 64 can be of the same material or different, depending on the assembly methods that are used and the ultimate end use of the product.

When blanks 12 and 112 are secured together, the elastomeric strips which act as securement means also provide additional stretchability in the leg area as well as providing a liquid-impervious barrier around the leg apertures. Extruded beads of an elastomeric composition such as gum rubber and the like, suitably secured to blanks 12 and 112, can also be used to this end.

The outermost of the two blanks, i.e., the blank which ultimately defines the outer surface of the training panty of this invention, preferably has different moisture permeability characteristics from those of the blank which defines the innermost layer of the training panty. The former can be provided with an inherent moisture barrier which can be sprayed on or incorporated into the web from which the blank is cut during the manufacture thereof by appropriate use of fibers, binders and/or surfactants. The latter, i.e., the innermost blank, on the other hand is preferably non-wettable albeit moisture permeable. Again the desired non-wettability and moisture permeability characteristics can be obtained by suitable selection of fibers, binders, and/or surfactants during web manufacture.

If desired, an absorbent inner layer 66 of hydrophilic foam or unbonded cellulosic fluff can be disposed in the crotch area or portion 16 of blank 12. As shown in FIG. 6, the midportion of absorbent inner layer 66 can be contoured to substantially the same configuration as crotch portion 16 of blank 12. Absorbent inner layer can also have an upper portion 68 which extends over a part of front panel 14 of blank 12, crotch portion 70 which is longitudinally coextensive but horizontally non-coextensive with crotch portion 16 of blank 12 and lower portion 72 which extends over a part of back panel 18 of blank 12. However, it is to be understood that the absorbent inner layer can have any desired configuration and can be, for example, substantially coextensive with blank 12 or can be located simply in the crotch area or portion 16.

If absorbent inner layer 66 is disposed in the crotch area or portion 16 of blank 12 before blank 112 is superimposed thereon, it is not necessary to adhere the absorbent inner layer 66 to the blank 12. However, adhesive can be used if additional securement is desired.

Referring now to FIG. 7, when baby panty 1 is assembled, a second blank substantially identical in configuration to blank 12 is superimposed over blank 12. For purposes of clarity the second blank will be hereafter identified as blank 112 and the blank elements corresponding to the same elements of blank 12 will be identified by 100-series legends having the same last two digits. The blanks are superimposed so that the puffy surface of blank 112 faces and is juxtaposed to the exposed puffy surface of blank 12. When blanks 12 and 112 are superimposed, margin 26 of blank 12 extends beyond adjacent margin 128 of blank 112 and margin 32 of blank 12 extends beyond adjacent margin 130 of blank 112. Similarly, margin 126 of bland 112 extends over margin 28 of blank 12 and margin 132 of blank 112 extends over margin 30 of blank 12.

Elastic strips 47 and 44 are pre-stretched on blank 12 and secured to form gathered rear waistband section 6 and front waistband section 5. Tabs 46, 48, 50 and 52 are then preferably cut off. When strips 47 and 44 are thermoplastic, securement by heat sealing is the method of choice. The preferred method of heat-sealing is by intermittent heat-seal regions which provide ridges simulating stitching in the finished waistband.

In FIG. 3, training panty 100 is made of similarly contoured blanks as training party 1 but the thermoplastic heat-sealable elastic material 101 utilized in the waistband of panty 1 is also utilized to provide self-fitting leg apertures 102 and 104 of training panty 100. FIG. 4 depicts training panty 106 which is similar to training panty 1 but wherein continuous hot-melt elastic bead 107, 103, and 105 is used to enhance stretch in the waistband area 108 as well as in the leg areas 110 and 111.

Side seams 7 and 8 can be formed in several ways. The preferred construction is shown in FIG. 8. Longitudinal side margins 28 and 130 of blanks 12 and 112 respectively are butted together. Margin 32 of blank 12 is then lapped over abutting margins 28 and 130 on one side and margin 126 is lapped over the same abutting margins on the other side to form side seam 7 (FIG. 2) which is sealed with additional glue lines 80 and 86. Similarly, the seam on the opposite side of the panty, i.e., seam 8, is formed by abutting margin 30 with margin 138 and then lapping over the abutting margins, margin 26 on one side thereof and margin 132 on the other side thereof, and by securing the lapped margins by means of glue lines 82 and 84. Such a side seam construction provides a side seam that is only three layers thick. As can be seen from FIGS. 5, 6, 7 and 8, while the blanks that are utilized to form a training panty having the preferred seam construction are asymmetric as discussed in detail hereinabove, the glue lines such as lines 54, 56, 58, 60, 62 and 64 that are laid down or extruded onto blank 12 during the assembly process are symmetric with respect to longitudinal centerline 24. That is, glue lines 56 and 58 are closer to the respective outermost edges of margins 28 and 30 than are glue lines 54 and 60 relative to respective margins 26 and 32.

Since the fabric to adhesive bond is weaker than the fabric itself, the preferred seam construction described hereinabove and illustrated in FIG. 8 permits the panty to be torn apart at the seams for easier removal when the panty is soiled.

Referring to FIGS. 14 and 15, the panty side seams can alternatively be constructed by alternatively lapping margins 26, 30, 126 and 130 or by lapping margins 26 and 126 over sandwiched edges 30 and 130, it being understood that margins 30 and 130 could overlie sandwiched margins 26 and 126 and the order of lapping illustrated in FIG. 14 could be reverse, if desired. The seam is then secured with glue lines such as lines 81, 83, 85 and 87 in FIG. 14 and glue lines 88, 90, 92, 94 and 96 in FIG. 15. An asymmetric blank is not necessary for the latter two seam constructions.

When the panty is worn, the ribbed surface such as surface 38 in FIG. 9 of one of the blanks faces the baby and forms the panty inner surface and similar ribbed surface of the other blank forms the outer surface of the panty. The puffed surfaces such as surface 40 in FIG. 10 face one another.

In an alternate embodiment, as shown in FIG. 11, the training panty of this invention can be constructed from a single blank 212 of microleated, cross-compacted fabric which is provided with side margins 226, 228, 230 and 232 as well as opposed oblong cut-outs 220 and 222. Elastomeric strips 242 and 244 are laid down as described in connection with FIG. 5, with tabs 246 and 248 extending from side margins 226 and 228, respectively, of blank 212 and tabs 250 and 252 extending from sides 20 and 232, respectively. Edges 234 and 236 are folded over strips 242 and 244, respectively, as shown in FIG. 11, and sealed as described hereinabove to provide waistband front and rear portions 260 and 262, as shown in FIG. 12. Tabs 246, 248, 250 and 252 are cut off, blank 212 is folded, and edges 228 and 232, and 226 and 230 are overlapped and secured.

Referring to FIG. 13, if desired, an absorbent layer of panel 264, enveloped in or covered with a moisture-pervious facing if desired, can be placed in the crotch area 216 of blank 212 and sealed thereto by heat-sealable adhesive strips 266 and 268, in the area of oblong cutouts 220 and 222, before formation of the side seams.

A further embodiment is shown in FIG. 17. In constructing a training panty in accordance with this invention, a contoured blank 312, as shown in FIG. 17, is positioned so that the puffy surface 340 faces upwardly as described hereinabove. A non-contoured, horizontally non-coextensive facing layer 300 having a rectangular configuration overlies the longitudinal midportion of blank 312 so that the front waistband edge thereof is aligned with waistband edge 334 of blank 312 and the rear waistband edge thereof is aligned with waistband edge 336 of blank 312. Facing layer 300 is, of course, moisture-permeable, and an absorbent panel can be sandwiched between facing layer 300 and blank 312 which in this case forms the backing layer. The absorbent panel in this case extends from about the waist region of front portion of the undergarment defined by panel 314 to the waist region of back portion of the undergarment defined by panel 318. A portion of the waistband of the panty (not shown) can be gathered to enhance fit, if desired. Similarly, beads of an elastomeric thermoplastic material can be laid down along the leg cutouts 320 and 322 to provide a gasket around the leg apertures of the produced training panty.

The outer ply of the undergarments of this invention can be inherently hydrophobic as manufactured. On the other hand, the outer ply can be an inherently hydrophilic web which is treated so as to be moisture-repellent or moisture-impervious, for example, by spraying the outerlayer with a hydrophobic agent. Suitable agents include the cellulose-reactive sizing agent emulsions like those sold by Hercules, Inc. under the tradename "Aquapel" and the like. A stretchable plastic film can additionally be provided overlying the outer ply as an additional mositure barrier, if desired.

Preferably the facing layer of the undergarment, i.e., the layer contacting the wearer's skin, is non-wettable even though this layer is moisture permeable. To this end the facing layer can be made of a non-woven fabric which contains synthetic hydrophobic fibers or hydrophobic binders for the non-woven fabric, or the layer can be treated before or during undergarment manufacture with small amounts of a suitable hydrophobic agent. Preferred webs are those disclosed in U.S. Pat. No. 3,663,348.

Referring now to FIGS. 18-22, a further embodiment of the training pants is disclosed therein which is similar in many respects to the previously described embodiments, but which differs therefrom in terms of materials, shape and the like, as will hereinafter appear. As with the previously described embodiments, panty 400 includes a first or inner layer 401 adapted to be positioned against the skin of the wearer, and a second or outer layer 402 similar in size and shape to layer 401. As is evident from FIG. 20, layer 402 includes parallel and edges 403 and 404, with end edge 403 adapted to be disposed about the back of the infant, and with end edge 404 being adapted to be positioned at the infant's stomach. The side edges of blank 402 converge from edge 403 toward edge 404 and include a rectilinear section 405 adjacent edge 403 and a rectilinear section 406 adjacent edge 404. The side edges are recessed between rectilinear sections 405 and 406 so that the layer is somewhat hourglass shape, and to define a crotch section 407 of reduced width. The crotch section 407 is comprised of a rectilinear section 408 merging with an arcuate section 409 adjacent edge section 405 and a further arcuate section 410 adjacent edge section 406. It will be understood that layer 401 is shaped identically with layer 402, and superimposed thereover, a is evident from FIG. 21.

Edges 405 and 406 have the same length, so that when the panty 400 is manufactured, the layers 401 and 402 are folded about their mid-portion and edges 405 and 406 are brought into juxtaposition with one another and joined, as will be hereinafter described in detail, to produce a finished garment wherein the seams 411 are disposed in front, rather than at the sides, as is evident from FIGS. 18 and 19. The seam location is an important aspect of the embodiment of FIGS. 18-22, since the front location, as shown in the drawings, is in an area of minimum stress, thus contributing to the stability and longevity of the product.

As with the previously described embodiments, first layer 401 is moisture permeable to permit excreted body fluids to pass therethrough, in the event that a training infant has an accident. Second layer 402 has hydrophobic characteristics, particularly as compared to layer 401, and may be moisture repellent so as to maintain excreted body fluids within the interior of the training panty. If desired, an absorbent layer 412 may be disposed between layers 401 and 402 for absorbing and retaining excreted body fluids. As will be well understood by those skilled in the art, layer 412 may be a batt of wood pulp fibers, cotton linters, synthetic wood pulp, plural layers of tissue or wadding, etc. When layers 401 and 402 are formed of mechanically compacted non-woven fabrics of the type described above, it is not necessary to secure layer 412 to the adjacent layers, since layer 412 will be held in place by friction. However, when layer 402 and/or layer 401 is formed of a plastic sheet of the type hereafter described, or if it is simply desired to prevent layer 412 from moving relative to layers 401 and 402, securement means, such as a suitable hot melt adhesive, may be utilized, as will be readily apparent to those skilled in the art.

As is evident from FIG. 20, absorbent layer 412 may include parallel end edges 413 and 414, with edge 413 being longer than edge 414, and with edges 413 and 414 being disposed in parallel adjacency with edges 403 and 404 of the inner and outer layers of the panty, respectively. Layer 412 includes parallel, rectilinear side edges 415 adjacent end edge 413, and rectilinear side edges 416 adjacent end edge 414. Edges 416 are disposed at an angle with respect to one another, and generally parallel to edges 406 of layer 402. The sides of panel 412 further include edges 417 which converge toward one another from the ends of edges 415, and which merge with arcuate sections 418 that join edges 416. Absorbent layer 412 is centered with respect to blank 401 and 402, as can be best seen in FIG. 20.

In order to provide a mechanism for wicking absorbed liquids to a remote area of absorbent layer 412, the layer may be sprayed with water and embossed in accordance with the teachings of Burgeni U.S. Pat. No. 3,017,304 to provide one or more longitudinally extending lines 419, and a plurality of lines 420 disposed at an angle with respect to line(s) 419. It will be understood that lines 419 and 420 cooperate to define a wicking network for transporting absorbed liquid to remote areas of the absorbent layer 412, so as to best utilize the entire absorbent capability of layer 412.

For improved fit, the panty 400 is provided with a gathered waistband portion 421, and elaticized leg openings 422. The gathered waistband portion 421 provides snug fit about the infant's waist, and the elasticized, but ungathered, leg openings provide a yieldable comfortable fit about the infant's legs. To provide the gathering in the waistband area, stretch elements 423 and 424 are provided between the ends of the inner and outer layers and the ends of the absorbent layer at the rear and front of the garment, respectively. Elements 423 and 424 are secured to one or both of the adjacent layers in a stretched condition, and are then permitted to relax to elastically gather the layers 401 and 402, as is shown in FIG. 21.

The term "elastic," as used herein, refers to sheets, films, ribbons and the like which have a recovery of at least 90 percent, when elongated to within 10 percent of their yield point and measured in accordance with the following formula:

$$\text{Percent retraction} = \frac{L_e - L_t}{L_e - L_o} \times 100$$

where
$L_o$=original length of sample
$L_e$=fully extended length
$L_t$=length of sample measured 3 seconds after released from extended length.

The thickness of the elastic member generally is 10 mils or less, and preferably about 0.5 to about 5 mils. The elastic member has a recovery at 50 percent elongation after 3 seconds and preferably instantaneously of at least about 90 percent, and preferably close of 100 percent. For ease of stretchability, the modulus of elasticity of the elastic member at 50 percent elongation should not exceed about 2000 pounds per square inch. The modulus of elasticity is preferably substantially less than 2000 pounds per square inch, and most preferably is about 20 to about 200 pounds per square inch.

Elastic film members suitable for the training pants contemplated herein can be extruded to the desired thickness utilizing unvulcanized, thermoplastic compositions which are made up of an elastomeric component and an optional compatible modifier which is a thermoplastic polymer of a relatively low molecular weight but solid at ambient temperature.

Illustrative of the elastomeric components suitable for present purposes are block copolymers which comprise terminal thermoplastic polymer blocks and at least one non-terminal or intermediate elastomeric polymer block. Block copolymers of this general type may be prepared using a step-wise polymerization initiator, e.g., an organolithium compound. Such block polymerization techniques are well known in the art.

The elastomeric component can be linear or radial $A^1$—B—$A^2$ block copolymers or mixtures thereof with simple $A^1$—B block copolymers where $A^1$ and $A^2$ can be alike or different and represent a thermoplastic polymer block, such as poly (vinyl arene) block, and B represents an elastomeric polymer block such as a conjugated diene or a lower (i.e., $C_1$-$C_4$) alkene. The modifier component is a low molecular weight thermoplastic polymer having an average molecular weight of about 500 to about 7,500 and is present in the composition in an amount of about zero to about 200 parts by weight per 100 parts by weight of the elastomeric component.

A preferred thermoplastic film composition for the elastic film members comprises an elastomeric component which contains, as a major constituent thereof, as unvulcanized linear block copolymer of the general configuration

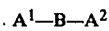

$A^1$—B—$A^2$ wherein $A^1$, $A^2$ and B have the same meaning as hereinabove. In these block copolymers the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to about 200 parts by weight per 100 parts by weight of the elastomeric component.

The preferred $A^1$—B—$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6000, preferably in the range of about 8000–30,000, and the A-blocks constitute about 5–50 percent, preferably about 10–30 percent, by weight of the block copolymer. The average molecular weight of the B-blocks for linear $A^1$—B—$A^2$ block copolymers preferably is in the range of about 45,000–180,000 and that of the linear copolymer, itself, preferably is in the range of about 75,000–200,000. The average molecular weight of the radial $A^1$—B—$A^2$ block copolymers preferably is in the range of about 125,000–400,000. The term "linear block copolymer" (or copolymers) includes branched $A^1$—B—$A^2$ copolymers as well as unbranched $A^1$—B—$A^2$ copolymers.

The radial $A^1$—B—$A^2$ copolymers useful for manufacture of elastic members for diapers of this invention are of the type described in U.S. Letters Pat. No. 3,281,383 to Zelinski et al. and conform to the following general formula: (A—B—)$_n$X, wherein A is a thermoplastic block polymerized from styrene or styrene homologues, B is an elastomeric block derived from conjugated dienes or lower alkenes, as indicated above, X is an organic or inorganic connecting molecule, with a functionality of about 2 to 4 as described in U.S. Pat. No. 3,281,383, or possibly with a higher functionality as described in the article entitled "New Rubber is Backed by Stars" appearing on page 35 of the June 11, 1975 issue of *Chemical Week*. As used hereinabove, "n" has a value corresponding to the functionality of X.

The preferred elastic film member is highly thermoplastic and, though elastomeric, is unlike rubber in that the film exhibits a relatively sharp melting point and is capable of being heat shaped. Also, the elastic film member can form permanent heat seals to substrates such as non-woven fabrics, or the like, at relatively low heat sealing peak temperatures, generally not above about 350° F. The film member is highly elastic and has a relatively low rubber modulus, i.e., it exhibits in at least one direction an elastic recovery from 50 percent stretch to at least 75 percent, preferably at least about 80 percent, and a 50 percent rubber modulus of not above about 2000 pounds per square inch, preferably not above 1000 pounds per square inch at 50 percent elongation. The film member also is very flexible, extensible and soft and normally exhibits a Gurley stiffness of about one or less at a film thickness of one mil, and an elongation to break of at least about 300 percent, preferably at least about 400 percent, in at least one direction at ambient temperatures.

When stretch members 423 and 424 are formed of a thermoplastic elastic material, they may be conveniently secured in place ultrasonically, such as by the use of apparatus of the type that is commercially available from Branson Instruments, Incorporated of Stanford, Connecticut. Such apparatus conventionally includes an anvil and a horn that are positioned in juxtaposed relationship to one another, and the parts to be joined are inserted therebetween. The horn is energized to transmit vibrations in the ultrasonic frequency range into the parts to be joined. In the present instance, the stretch elements 423 and 424 are elongated between layers 401 and 402, and the layers placed between a horn which coacts with an anvil which moves in registration with the product to provide a plurality of spaced rows of simulated stitching. In this regard, the anvil of the ultrasonic sealing apparatus preferably is provided with a plurality of spaced land areas so that the stretch elements are secured in place by a plurality of spaced securement zones. The securement zones, or welds, serve to retain the stretch elements in place by virtue of the sonically induced heat softening, or melting, not only the stretch elements themselves, themselves, but also of the thermoplastic fibers in the inner and/or outer layers.

Stretch and recovery is provided in the leg openings 422 by elastic elements 426, which extend generally parallel to side edge portions 408, 409 and 410, as can be best seen in FIG. 20. As noted above, elastic members 426 may be secured in place by sonic sealing and it is preferred that these elements be secured in place in a relaxed state so that the leg openings 422 can stretch and recover and apply a light compressive force about the thighs of the infant.

Side seams 411 are preferably effected by strips 427 of heat-sealable material disposed adjacent edges 405 and 406 and between layers 401 and 402. Heat sealable strips 427 may also be formed of a thermoplastic material, which may or may not have elastic characteristics, and which is sonically sealed in place.

With reference to FIG. 20A, two different forms of sonic sealing patterns are shown therein as being illustrative of the principles of the present invention. Referring first to elastic element 426, it will be noted that two sonic sealing lines are illustrated, each being generally sinusoidally shaped and parallel with one another. Each line is comprised of a plurality of spaced seal zones 428 in the illustrated embodiment, although it is also contemplated that continuous sonically induced welds may be provided if a sine pattern is utilized since the lines themselves are capable of elongation. With reference to strip 427, it is to be noted that each line of sonic welding includes a plurality of spaced weld zones 429, and that the resulting lines are spaced from, and parallel with one another and with the edges of strip 427. It should be noted that either form a plural sonic welding lines can be used for stretch elements 423 and 424, and whatever form of sonic welding pattern is utilized, it is important that the sonic welds themselves be spaced inwardly from the edges of the thermoplastic material so as to prevent tearing of the material.

Figure 22B:
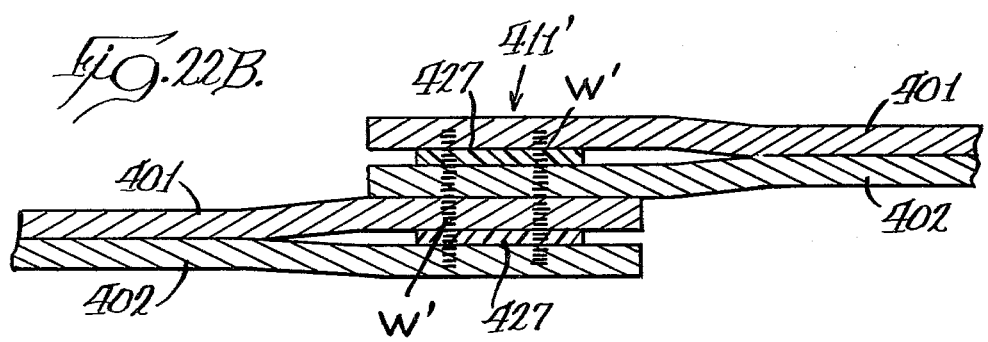
Figure 22C:
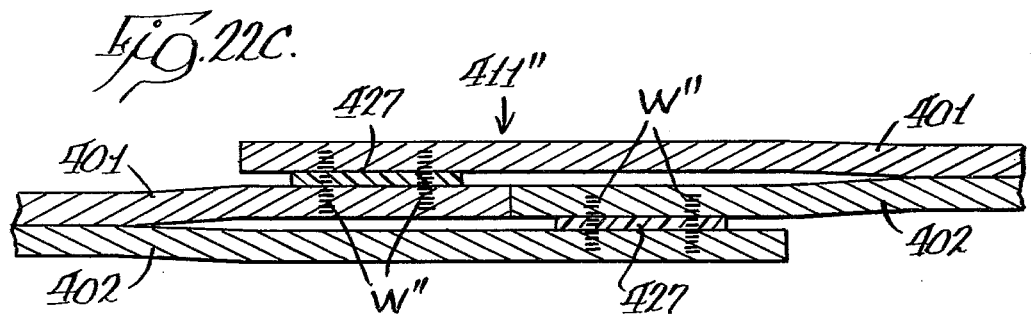

The seams in the panty garment can be formed in a variety of fashions, three of which are illustrated in FIGS. 22A, 22B, and 22C. In FIG. 22A the ends of layers 401 and 402 are interleaved with one another and joined together by weld lines W, which as mentioned above may be a series of spaced sonic welds, to form seam 411. FIG. 22B illustrates a lap form of seam 411′ where the overlapping layers are secured together by weld lines W′. FIG. 22 C illustrates a butt type seam 411″, which is comprised of only three material thicknesses in the seam area, and wherein the layers are held together by weld lines W″.

As noted above, to provide the desired fit characteristics, layers 401 and 402 are mechanically compacted in at least one direction (widthwise as shown in FIGS. 20 and 21) so that the elastic members 423 and 424 can effectively gather the panty. While micropleating is the presently preferred form of mechanical compaction, other well known techniques, such as micrexing, may also be utilized. Layers 401 and 402 are preferably non-woven fabrics that include thermoplastic fibers in an amount and distribution such that the thermoplastic fibers heat soften, or melt, upon application of sonic energy and fuse to themselves and/or other non-thermoplastic fibers thereby creating bonded zones which retain the layers of the panty together. Many fabrics are capable of being compressively shrunk and sonically sealed, and the fabric containing a 50—50 polyester-rayon blend as described in U.S. Pat. No. 3,815,602 is illustrative. Non-woven polyester fabrics having fabric weights in the range of about 0.5 to 1.5 oz./yd$^2$ prior to compressive shrinking and containing at least 50% polyester fibers are preferred.

While specific non-woven fabrics have been illustrated and described, the present invention is not limited thereto, and layers 401 and 402 may be formed of other non-woven fabrics or even plastic sheet materials. Of course, if inner layer 401 is formed of a plastic sheet material, it would be perforated to permit excreted body fluids to pass therethrough. A moisture repellent outer layer 402 is particularly important for an overnight panty to prevent soilage of bed cloths in the event that a training infant has an accident. Plastic films of the type described in U.S. Pat. No. 4,036,233 are well suited for the purposes of the present invention, and it is also contemplated that such films be embossed for improved comfort and feel. In the event that a plastic film is not utilized as the outer layer and a non-woven fabric is utilized, the binder-surfactant ratio is controlled to give the fabric repellent characteristics. If the panty includes an absorbent layer, the side thereof adjacent outer layer 402 may be provided with one or more plies of repellent tissue (or the fibers on that side of the layer may be treated to be repellent) to provide an additional moisture barrier. As noted above, such a panel preferably includes wicking lines or channels, which also serve to reinforce the absorbent layer. Panels having a total panel weight of from about 9 to about 40 grams are presently contemplated.

If a moisture barrier in the form of a plastic film is incorporated in the panty of the present invention, it is also contemplated that this layer be provided in the interior of the product, and that both the inner and outer layers be non-woven fabrics, so that the panty will have a cloth-like appearance and feel.

By virtue of the contemplated method of manufacture, elastic members 423 and 424 may be stretched differentially, although it is presently contemplated that such members will be stretched equally during manufacture and apply the same gathering force during use. While elastic members 423 and 424 (and elements 426 and 427) have been illustrated and described as being relatively wide and solid members, the present invention also contemplates that such members may be reticulated, or comprised of narrow bands or monofilaments. It should be noted that in addition to providing a recovery force, members 423, 424, 426 and 427 also provide reinforcement at the borders of the panty and around the limb openings. While the elastic members have been described as being sonically sealed to the inner and outer layers, it is also contemplated that strips of an elastomer, such as rubber, could be sealed in place by intermittent application of a suitable hot-melt composition. In the event that the elastic members have anisotropic stretch characteriscs elements 423 and 424 are arranged so as to exert maximum stretch parallel to the adjacent edges of layers 401 and 402, while elements 426 are arranged to exert maximum stretch in direction perpendicular thereto.

With the blank configuration of FIG. 20, in a panty wherein layers 401 and/or 402 are a micropleated non-woven fabric of the type described above, extensibility is provided at the leg opening 422 and the relaxed elastic members 426 assist in recovery of the micropleated fabrics after extension.

In the event that seams 411 are heat sealed the panty may be removed by tearing it adjacent to the seams. It is also contemplated that the seams may be closed by an appropriate adhesive, tapes like those now used in disposable diapers, reclosable mechanical fasteners such as Velcro and other means that will occur to those skilled in the art.

The foregoing description and the drawings are intended as being illustrative and are not to be taken as limiting. Still other variations within the spirit and scope of this invention are possible and will present themselves to one skilled in the art.

What is claimed is:

1. A stretchable, integral blank of non-woven fabric suitable for forming a disposable undergarment, said blank being cut to define a front panel, a rear panel, and a crotch portion therebetween having first and second longitudinally oblong opposed cut-outs symmetrically situated on opposite sides of the longitudinal center line of said blank; each of said cut-outs extending from said front panel to said back panel along each longitudinal side margin of said blank; the radius of curvature of each said cut-out near the front panel being smaller than the radius of curvature of said cut-out near the back panels; said blank having an extensibility to failure of at least about 40 percent along the longitudinal center line of said blank and at least about 30 percent in the direction substantially normal to said longitudinal center line; said blank having a ribbed surface on one face thereof and a puffed surface on the other face thereof; and said front panel and said rear panel being asymmetrically positioned with respect to the longitudinal center line of said blank.

2. The blank of claim 1 wherein said extensibility to failure is greater than about 60 percent in a direction substantially parallel to the longitudinal center line and greater than about 55 percent in a direction substantially normal to said longitudinal center line.

3. The blank of claim 1 wherein said front and rear panels are of substantially the same width but are off-set relative to one another and with respect to the longitudinal center line of said blank.

4. A unitary, multilayer, disposable undergarment, suitable for use in training infants or by incontinent children or adults, which is constructed from a non-woven stretchable fabric and comprising a front portion, a rear portion, and a crotch portion connecting said front and rear portions; both side margins of said front portion being joined to respective side margins of said rear portion so as to define a self-fitting waist portion and self-fitting leg apertures, said undergarment having a moisture-pervious fabric inner layer adapted to contact the wearer's skin and which is stretchable through its area, a moisture-impervious outer layer which is stretchable throughout its area, and an intermediate liquid absorbent panel disposed therebetween, said inner and outer layers being micropleated with the micropleats being disposed generally perpendicularly with respect to said front and rear portions, said undergarment having an extensibility to failure of at least about 40 percent along the longitudinal center line of said front and rear portions and an extensibility to failure of at least about 30 percent in the direction substantially normal to said longitudinal center line.

5. The disposable undergarment of claim 4 wherein said extensibility to failure along the longitudinal center line of said front and rear portions is greater than about 60 percent and the extensibility to failure is greater than about 55 percent in the direction substantially normal to said longituidnal center line.

6. The disposable undergarment of claim 4 wherein said stretchable fabric is compressively shrunk perpendicular to the machine direction of the fabric and is provided with micropleats extending substantially normal to the machine direction of the fabric.

7. The disposable undergarment of claim 4 wherein the inner layer and the outer layer of said undergarment are joined to one another around the apertures by thermoplastic elastomeric beads.

8. The disposable undergarment of claim 4 wherein the self-fitting waist aperture is defined by transverse edges of the front portion and the rear portion and wherein an elastomeric member is secured between the inner and outer layers of the front and rear portions.

9. The disposable undergarment of claim 8 wherein the elastomeric member is a strip of a thermoplastic elastomer which joins adjacent regions of the inner and outer layers.

10. A unitary, multilayer, disposable undergarment, suitable for use in training infants or with incontinent children or adults, constructed from a non-woven micropleated, cross-compacted fabric, and comprising a front portion, a rear portion, a crotch portion connecting said front portion and said rear portion, and first and second side seams defining a self-fitting waist aperture and self-fitting leg apertures, said undergarment having a moisture-pervious inner layer adapted to contact the skin of the wearer, a moisture-impervious outer layer, and an intermediate liquid-absorbent panel disposed therebetween; micropleats in said fabric running parallel to the longitudinal center line of said front and rear portions of said undergarment and said fabric being more extensible in a direction substantially normal to said longitudinal center lines.

11. The undergarment defined in claim 10 wherein the front panel and rear panel of each layer is of substantially the same width but are off-set with respect to one another, wherein the front portion and the rear portion of the undergarment each comprise two juxtaposed front panels and rear panels, respectively; said panels being positioned so that one longitudinal side margin of each panel extends beyond the adjacent side margin of the panel in juxtaposition therewith, and further so that at said side seams one side margin of one inner panel abuts one side margin of one outer panel and the resulting abutment is overlapped on both sides by the nearest side margins of the other inner panel and the other outer panel.

12. The undergarment defined in claim 11 wherein each of said side seams is three layers in thickness.

13. The undergarment defined in claim 10 wherein each of said side seams is four layers in thickness.

14. A disposable undergarment which comprises an integral blank of a stretchable non-woven fabric and defining a front portion, a back portion, and a crotch portion connecting the front portion with the back portion; said crotch portion being provided with opposed longitudinally oblong cut-outs, said blank being folded over so as to align the transverse margin of the front portion with the transverse margin of the back portion, the side margins of the front portion being joined to the side margins of the back portion so as to define a waist aperture and a pair of leg apertures, and an elastomeric member being secured around at least a portion of said waist aperture so as to gather the fabric of at least one of said portions; said blank being formed of a fabric having micropoleats throughout its area wherein the micropleats run generally parallel to the longitudinal center line of said front and rear portions and having an extensibility to failure of at least about 40 percent along the longitudinal center line of said front and back portions and an extensibility to failure of at least about 30 percent in the direction substantially normal to said longitudinal center lines.

15. The disposable undergarment defined in claim 11 wherein an absorbent panel is positioned within said undergarment at least in the crotch portion thereof.

16. The disposable undergarment defined in claim 15 wherein said absorbent panel extends over at least a portion of said front and back portions.

17. The disposable undergarment defined in claim 15 wherein said absorbent panel extends from the waist region of the front portion to the waist region of the back portion.

18. The disposable undergarment defined in claim 17 wherein said absorbent panel is covered with a facing layer.

19. A disposable undergarment comprising a first layer adapted to be positioned adjacent the wearer's skin, said first layer being a moisture-permeable non-woven fabric formed from a blank having a front portion, a rear portion, and a crotch portion of reduced width between said front and rear portions, said moisture permeable non-woven fabric being compacted in a direction normal to a longitudinal center line extending between said front and rear portions so as to provide an extensibility to failure of at least about 30 percent, said first layer being micropleated throughout its area with the micropleats running generally parallel to the longitudinal center line of said front and rear portions, said first layer including a puffed surface and a ribbed surface with the ribbed surface being adapted to contact the wearer's skin; a second layer adapted to be disposed outwardly when the undergarment is worn, said second layer being dimensionally similar to said first layer and positioned in superimposed relationship with respect thereto, said second layer having stretch characteristics similar to those of said first layer and said second layer being more moisture repellent than said first layer; means securing peripheral portions of said first and second layers to one another; and means securing the front and rear portions of said layers to one another on opposite sides of said crotch portion to complete the undergarment.

20. The disposable undergarment of claim 19 wherein said second layer is a non-woven fabric mechanically compacted in a direction normal to the longitudinal center line extending between its front and rear portions to provide an extensibility to failure of at least 30 percent.

21. The disposable undergarment of claim 19 wherein said second layer is an elastic thermoplastic film.

22. The disposable undergarment of claim 19 wherein said first layer is provided with a plurality of substantially parallel micropleats and said micropleats run substantially parallel to the longitudinal center line of said first layer.

23. The disposable undergarment of claim 19 wherein said means securing peripheral portions of said first and second layers to one another include strips of elastic material secured in a stretched condition between peripheral portions of said layers.

24. The disposable undergarment of claim 23 wherein said strips of elastic are secured between peripheral portions of said layers by adhesive means.

25. The disposable undergarment of claim 23 wherein said layers have thermoplastic properties and said strips of elastic material are thermoplastic and are intimately bonded to said layers.

26. The disposable undergarment of claim 25 wherein said strips are intimately bonded to said layers at spaced locations.

27. The disposable undergarment of claim 26 wherein the bonds at said spaced locations are defined by resolidified thermoplastic material heat softened by the application of ultrasonic energy.

28. The disposable undergarment of claim 19 wherein the means securing the front and rear portions of said layers to one another on opposite sides of said crotch portion include strips of elastic material bonded to said layers in a stretched condition.

29. The disposable undergarment of claim 28 wherein said layers have thermoplastic properties and said strips of elastic material are thermoplastic and are intimately bonded to said layers.

30. The disposable undergarment of claim 29 wherein said strips are intimately bonded to said layers at spaced locations.

31. The disposable undergarment of claim 30 wherein the bonds at said spaced locations are defined by resolidified thermoplastic material heat softened by the application of ultrasonic energy.

32. A disposable undergarment comprising a first layer adapted to be positioned adjacent the wearer's skin, said first layer being a moisture permeable non-woven fabric formed from a blank having a front portion, a rear portion, and a crotch portion of reduced width between said front and rear portions, said moisture permeable non-woven fabric having discontinuous micropleats extending generally parallel to a longitudinal center line extending between said front and rear portions so as to provide an extensibility to failure of at least about 30 percent, said micropleats defining a ribbed surface on one side of said non-woven fabric and a puffed surface on the opposite side of the non-woven fabric; a second layer adapted to be disposed outwardly when the undergarment is worn, said second layer being dimensionally similar to said first layer and positioned in superimposed relationship with respect to the puffed surface of said non-woven fabric, said second layer having stretch characteristics similar to those of said first layer and said second layer being more moisture repellent than said first layer; an absorbent panel disposed between said first and second layers in the crotch portion thereof; means securing peripheral portions of said first and second layers to one another; gathering means associated with the ends of said front and rear portions for providing a self-fitting body aperture; and means securing the front and rear portions of said layers to one another on opposite sides of said crotch portion to complete the undergarment.

33. The disposable undergarment of claim 32 wherein said non-woven fabric has between 8 and 20 rows of micropleats per inch.

34. The disposable undergarment of claim 33 wherein the front portion of said first layer is narrower than the rear portion thereof, whereby said means securing the front and rear portions of said layers to one another on opposite sides of the crotch portion defines seams that are disposed in the front of the undergarment when it is worn.

35. The disposable undergarment of claim 34 wherein said first and second layers are shaped generally in the form of a trapezoid, with the side edges thereof converging from the end of said rear portion to the end of said front portion.

36. The disposable undergarment of claim 35 wherein said reduced width crotch portion is defined by side edges of said layers, which converge from an arcuate junction with said rear portion toward an arcuate junction with said front portion.

37. A disposable undergarment including a waist encircling portion and leg openings and comprising: a moisture permeable first layer adapted to be positioned adjacent the wearer's skin; a second layer adapted to be disposed outwardly when the undergarment is worn, said second layer being dimensionally similar to said first layer and positioned in superimposed relationship with respect to said first layer, said second layer being more moisture repellent than said first layer; one of said layers being a non-woven fabric having throughout its area discontinuous micropleats extending generally parallel to a longitudinal center line extending generally perpendicular to said waist encircling portion so as to provide an extensibility to failure of at least about 30 percent, said micropleats defining a ribbed surface on one side of said non-woven fabric and a puffed surface on the opposite side of the non-woven fabric; the other of said layers having stretch characteristics similar to those of said one layer; means securing said layers to one another to provide said waist encircling portion and said leg openings; and gathering means associated with the waist encircling portion and leg openings of said undergarment for providing self-fitting apertures.

38. The disposable undergarment of claim 37 wherein both of said layers are non-woven fabrics.

39. The disposable undergarment of claim 37 wherein said moisture permeable first layer is said non-woven fabric, and said second layer is disposed in superimposed relationship with respect to the puffed surface of said non-woven fabric.

40. The disposable undergarment of claim 37 wherein each of said layers includes a front portion, a rear portion, and a crotch portion connecting said front and rear portions; both side margins of said front portions being joined to respective side margins of said rear portions so as to define said self-fitting waist encircling portion and said self-fitting leg openings.

* * * * *